United States Patent [19]
Townley

[11] Patent Number: 6,136,034
[45] Date of Patent: Oct. 24, 2000

[54] ENARTHRODIAL TYPE JOINT SOCKET IMPLANT

[75] Inventor: Charles O. Townley, Port Huron, Mich.

[73] Assignee: BioPro, Inc., Port Huron, Mich.

[21] Appl. No.: 09/160,746

[22] Filed: Sep. 25, 1998

[51] Int. Cl.$^7$ ........................................... A61F 2/34
[52] U.S. Cl. ........................... 623/22.23; 623/22.11
[58] Field of Search ............................... 623/18–23

[56] References Cited

U.S. PATENT DOCUMENTS

| | | | |
|---|---|---|---|
| D. 249,957 | 10/1978 | Eicher et al. | 623/22 |
| 3,698,017 | 10/1972 | Scales et al. | 623/22 |
| 3,829,904 | 8/1974 | Ling et al. | 623/22 |
| 4,450,592 | 5/1984 | Niederer et al. | 623/22 |
| 4,883,491 | 11/1989 | Mallory et al. | 623/22 |
| 5,171,285 | 12/1992 | Broderick | 623/22 |
| 5,405,402 | 4/1995 | Dye et al. | 623/22 |

FOREIGN PATENT DOCUMENTS

| | | | |
|---|---|---|---|
| 120595 | 10/1984 | European Pat. Off. | 623/22 |
| 1334584 | 10/1973 | United Kingdom | 623/22 |
| 2052997 | 2/1981 | United Kingdom | 623/22 |

OTHER PUBLICATIONS

BioPro, Inc., "The Biopro Ceramic Tara," brochure, Oct. 1997.

BioPro, Inc., "PSL Total Hip Replacement System," brochures, 1991, re–published 1997.

Townley, Orthopedic Clinics of North America, vol. 13, No. 4, Oct. 1982, "Hemi and Total Articular Replacement Arthroplasty of the Hip with the Fixed Femoral Cup," pp. 869–894.

Jacobs, Transactions of the 24th Annual Meeting of the Society for Biomaterials, Apr. 22–26, 1998, San Diego, California, p. XLVII: "Wear—The Clinical Problem: Total Hip Replacement."

*Primary Examiner*—Bruce Snow
*Attorney, Agent, or Firm*—Christopher John Rudy; Andrew Joseph Rudy

[57] ABSTRACT

An enarthrodial type joint socket implant, for example, for total hip replacement, can contain a modified surface configuration of its cement-fixable outer wall having small, widely dispersed cement spacer elevation members, for example, rectangularly-oriented cement spacer elevation members in block form with dove tailed configurations, which are sufficiently high to provide an appropriately thick cement mantle to assure an optimally proficient implant-stabilizing cement mantle which is universally consistent and technically routine to implant. It can, in addition or independently, have, and this is especially pertinent to conventional hip replacement acetabular cup prostheses, a unique snap-fitted arrangement of the head-restraining marginal outlet of the acetabular component having posterior and anterior cut outs of the implant to avoid premature impingement against a prosthetic femoral neck, allowing a normal, non-dislocating range of unobstructed external and internal rotation of the hip, and a hood that is a marginally extended continuation of the superior one-half or so of the cup containment that is of a sufficient magnitude to reduce the overall dimension of the socket outlet to less than a hemisphere. The implant can be suitably adapted for use in other enarthrodial type joints such as the shoulder.

17 Claims, 3 Drawing Sheets

ENARTHRODIAL TYPE JOINT SOCKET IMPLANT

FIELD AND PURVIEW OF THE INVENTION

In general, the present invention concerns a plastic enarthrodial type joint socket implant, useful in arthroplasty. More particularly, it concerns certain innovative modifications in the polyethylene acetabular prosthesis which is commonly used to replace the socket side of the hip joint in total replacement arthroplasty, specifically designed for use without metal backing and employing a suitable cement such as a polymethylmethacrylate surgical cement to stabilize the replacement component. As an implant for conventional total hip replacement, for example, it can include some significant features: 1) a cementable outer surface with, for example, an array of protrusions, which set the to which the implant can be inserted into the acetabular preferably, the protrusions being of a dove tail type, with there being present a series of grooves in addition; 2) a snap-fitting inside cup containment which extends further than hemispherical about the corresponding implanted femoral ball so that dislocation is less apt to occur also has cut-outs in critical areas of the cup that provide for not only a nearly if not fully natural range of motion but also protection from leveraged dislocation. As an implant in conservative resurfacing arthroplasty, such as the for example, it generally would be able to include the cementable outer surface and cut-outs, appropriately adapted for such procedures.

EXPLANATION BY WAY OF BACKGROUND

Early on in the procedural history of total hip arthroplasty, all polyethylene acetabular replacement components were designed without metal backing and were routinely stabilized with cement. The outer cemented surface of the component was provided with shallow, cement-adhering irregularities of some sort, usually in the form of narrow and shallow circumferentially oriented channel indentations. The spherical prosthetic, head-containing dimension of the socket part of the implant was commonly limited to less than a hemisphere in the interest of avoiding premature, motion-induced abutment of the prosthetic femoral neck against an otherwise overly extended marginal outlet of the implant which would obstruct the functional range of rotational joint motion and induce the associated propensity for anterior or posterior dislocation of the replaced joint.

The not infrequent occurrence of latent procedural failure owing to implant loosening associated with degradation and separation of the cemented bone-prosthetic interface led to the introduction and subsequent use of metal-backed polyethylene acetabular components in the early 1980s for the intended purpose of ameliorating the incidence of this complication. The metal-backed part of the composite component was made available with either a porecoated acetabular interfacing surface that depended on latent bone growth to stabilize the prosthesis with the patient's acetabulum or without a porous coated surface that required cement fixation to provide implant stability.

In the meantime, the reduction in the spherical marginal extension of the implant to less than a hemisphere is, of course, accompanied by a commensurate reduction in the overall depth of the prosthetic head-constraining socket, and, consequently, the replaced hips remained vulnerable to the propensity for postoperative dislocation. Early in the 1970s, an attempt was made to counter this complication by extending the spherical continuation of the socket margin a bit beyond a hemisphere, i.e., sufficient enough to provide a snap-fitted containment with the prosthetic femoral head. In this initial concept of a snap-fitted articulation, the marginal extension was distributed evenly around the total circumferential margin of the socket outlet. As a consequence of problems that were associated with an articular constraining arrangement of this sort, the concept of a snap-fitted articulation was abandoned after a short period of use and was not again known to have been utilized prior to the present invention. However, the continuing problem of postoperative joint dislocation has been addressed more recently by other innovators who have designed the acetabular component with a superiorly positioned, non-snap-fitted marginal extension for the purpose of merely providing a structural block against dislocation.

Drawbacks to the heretofore listed, variable methods of designing and fixation of an acetabular replacement component are multifactorial and are generally enumerated as follows:

First, the nature and distribution of the shallow irregularities on the cemented outer surface of the polyethylene component makes it technically difficult, if not impossible, to assure a maximally efficient implant-stabilizing, bone-to-prosthesis cement mantle, i.e., a cement mantle that is symmetrically distributed to provide a consistently even and adequate thickness of cement throughout the total dimension of the bone-prosthesis interfacing interval.

Second, acetabular components which are designed with a femoral head-constraining marginal outlet that is reduced to less than a hemisphere are prone to postoperative dislocation. Although a relatively infrequent occurrence, postoperative dislocation of a replaced hip is an inordinately serious and disheartening complication. Aside from the severe discomfiting and emotional effect of the ordeal on the patient and surgeon alike, this complication has a substantial adverse impact due to the not insignificant costs associated with the required added surgical intervention and hospital care.

Third, polyethylene acetabular components that were designed with a complete circumferentially extended snap-in marginal outlet produced yet an earlier premature stage of marginal abutment against the neck of the femoral component, and an associated, commensurate reduction in the range of rotational motions, which in turn induce the propensity for a "leveraged-out" anterior or posterior joint dislocation, notwithstanding the snap-fitted arrangement. Furthermore, repetitive, motion-induced abutment between the femoral neck and the extended acetabular margin, particularly with rotary joint motions, resulted in erosive degradation of the repetitively traumatized, overextended margins of the acetabular cup outlet, consequentially producing yet another source for the proliferation and the associated detrimental effects of foreign body debris.

Fourth, cemented metal-backed acetabular components have had no demonstrable salutary effect on the incidence of implant loosening complications.

Fifth, long-term experience with the use of uncemented porecoated metal-backed components, although shown to be effective in stabilizing the implant, has demonstrated a substantive acceleration in the rate of polyethylene wear, and an associated significant increase in the incidence and severity of debris-induced periprosthetic osteolysis, occasionally with catastrophic consequences to the patient.

Sixth, the concept of a superiorly oriented, non-snap-fitted marginal extension of the implant, although reasonably effective in reducing the incidence of dislocation if properly aligned, is highly technique-dependent, i.e., relative to the appropriate rotational positioning of the extended head-restraining implant rim. This is specifically relevant to the inability to predetermine with any absolute degree of certainty as to whether a given hip is, or will be, vulnerable to an anterior versus a posterior joint dislocation. For instance, an inadvertent, erroneously suspected propensity for anterior dislocation that is managed by a precautionary antero-superiorly positioned rim extension may result in a marginally unguarded posterior dislocation, or vice versa.

It would be desirable to overcome such drawbacks and provide an improved socket implant, the lack and need for which is of long standing in the art. It would be further desirable to be able to apply improvements suitably to additional socket types.

INTRODUCTION TO THE INVENTION BY WAY OF A SUMMARY AND ELABORATION

In general summary, the present invention provides an improved enarthrodial type joint socket implant, useful in arthroplasty. In a particular embodiment, illustrative of the invention with a complement of beneficial features, it pertains to certain specific modifications in the design configuration of former and current other polyethylene acetabular hip components, for example, for total conventional hip replacement, which not only enhance the proficiency and longevity of the stabilizing bone-prosthetic cement mantle in the interest of extending the survivorship longevity of the acetebular component, relative to the time to failure of the arthroplasty procedure, but also provide a secure snap-fitted articulation that produces the desired effect of guarding against the propensity for postoperative dislocation while at the same time allowing for a normal functional range of motion of multi-planed joint motion.

The invention addresses or overcomes the foregoing drawbacks.

A first part of the present invention, in general, concerns a modified surface configuration of the cement-fixable outer wall of the component that is designed with small widely dispersed cement spacer elevation members to assure an optimally proficient implant-stabilizing cement mantle which is universally consistent in and technically routine to implant. The small spacing members may be of any configuration and vary in height so long as they are sufficiently high to provide an appropriately thick cement mantle. A preferred embodiment concerns rectangularly-oriented cement spacer elevation members in block form, with dove tailed configuration, which may be machined in, and which, aside from assuring an appropriately distributed cement mantle, also provides a more secure, interdigited physical fixation with the cementing material, for example, polymethacrylate.

A second general part of the invention, particularly pertinent especially to conventional hip replacement acetabular cup prostheses, can concern an innovative snap-fitted arrangement of the head-restraining marginal outlet of the acetabular component. One feature of this second general part of the invention pertains to posterior and anterior "cut outs" of the implant to particularly avoid premature impingement against the prosthetic femoral neck , thus allowing a normal, non-dislocating range of unobstructed external and internal rotation of the hip. Although, if left uncompromised, a reduction in the marginal extension of the implant rim in these areas would ordinarily provoke a propensity for dislocation, this has been effectively addressed by a second feature of this second general part of the invention. This second feature pertains to a marginally extended continuation of the superior one-half or so of the cup containment that is of a sufficient magnitude to reduce the overall dimension of the socket outlet to less than a hemisphere, which, as a consequence, reconstitutes the desired advantages of a snap-fitted articulation without incurring the aforementioned listed disadvantages associated with other attempts to provide a snap-fitted arrangement by the means of a complete, uninterrupted circumferential extension of the marginal head constraint.

Advantages of the aforementioned first general part of the present invention include the following: 1) the design-related improvement in the physical mode of cement fixation and the technical ease of providing an appropriate, evenly distributed and universally thick cement mantle should ameliorate, or at the least, decelerate, the process of implant loosening complications and prolong the time to failure of the acetabular component; 2) a commensurately thicker polyethylene component can be accommodated by eliminating the space-occupying thickness of a metal-backed container; and 3) a reduction in the rate of polyethylene wear and the associated incidence and severity of debris-induced periprosthetic osteolysis, a commonly cited cause of premature implant loosening and related complications. Also, 4) an ability to effectively employ a socket implant made solely of ultra high molecular weight polyethylene (UHMWPE), which, when cemented as the present invention can provide and eliminating metal-to-bone contact, may reduce the rate or incidence of implant loosening due to the substitution of the metal with the more resilient implant and cement, and consequent lessening of bone resorption at the implant-bone interface. In addition, 5) avoiding the use of expensive metal-backed part in the component substantially reduces the overall cost of the replacement procedure.

Advantages of the aforementioned second general part of the invention arise from the beneficial effect associated with the appropriately positioned marginal cut-outs and in addition the superior extension of the socket outlet in the prevention of dislocation. Aside from the provision for a snap-fitted socket arrangement, the superiorly oriented rim extension produces an appropriately localized and extended "hood" that, in an by itself, provides an effective mechanical block against either antero-posterior or postero-superior dislocation, which are the commonly encountered directional modes of this complication. Concurrently, the strategically positioned posterior and anterior cut-out indentations augment the avoidance of dislocation by allowing a normal range of anterior and posterior hip rotations.

Numerous further advantages attend the invention.

DRAWINGS OF THE INVENTION IN BRIEF

The drawings form part of the specification hereof. With respect to the drawings, the following is briefly noted.

DETAILED DESCRIPTION OF ILLUSTRATIVE EMBODIMENTS

The invention can be further understood by the present detail which may be read in view of the drawings. The same is to be taken in in an illustrative and not necessarily limiting sense.

Although the invention is described primarily with respect to and preferably is the hip, suitably adapted, it may be modified for use as another enarthrodial joint socket. For example, the joint of concern may be the shoulder.

With reference to the drawings, features generally common to socket implants of the invention 100 (FIGS. 1–7) and 200 (FIGS. 8–12) for total conventional (FIGS. 1–7) and TARA (FIGS. 8–12) hip replacements, which may be referred to as head-receiving socket implant cups 100, 200 include supporting body 101, 201 and articular surface 110, 210, which is smooth, and may have a 20-degree boundary chamfer 110C (FIG. 3), and a cementable, mountable back surface 120, 220. The articular surface 110, 210, when the cup 100, 200 is suitably mounted in suitable receiving stock such as human cotyloid cavity bone 7 such as by cementing with a methacrylate surgical cement 8, mates in articulating, gliding contact with the smooth external surface the femoral head implant when surgically mounted. Thus, the acetabular head-receiving cup 100, 200 can be provided with its outer, actabular-facing surface 120, 220 having built-in, dovetail-sided 121, 221 elevated block spacers 122, 222, which assure both an evenly distributed and concentrically thick cement mantle and, concurrently, a secure cement interdigited prosthetic surface. Central elevated block or button 123, 223, which may be circular and with or without grooves, also may be dovetailed. Grooveless, circumferential areas 124, 224 between the blocks 122, 222 may be present. Grooves 125, 225, for example, being about 0.020-inch in depth such as depicted with respect to the cup 100 in detail by depth 125D (FIG. 6) with a 0.015-inch radius such as depicted with respect to the cup 100 in detail by radius 125R (FIG. 6) in the bottom thereof, also can help in cementing.

Antero-inferior and postero-inferior marginal extensions of the implant component 100, 200 have been reduced by cut-out margins 126, 226 to not only accommodate the anterior anatomical indentation of the socket containment and avoid an unsupported, non-contained peripheral "hang-over" of the cup rim anteriorly which could compromise the latent stability of the cup 100, 200 but also to minimize the potential for premature abutment of the postero-inferior aspect of the rim against the opposing femoral neck with external rotation and/or adduction of the hip. The marginal rim cut-outs 126, 226 are angled, for example, the two rim cut-outs 126 can be at 30-degree angles. Appropriate intra-operative technical placement of the marginal rim cut-outs 126, 226 in relation to rim top 127, 227, which is angled, for example, with each of the rim tops 127, 227 at a 30-degree angle, may be assured by identifying the designated superiorly positioned rim of the component with a small, squared surface rim projection 127P.

Generally peculiar to the acetabular cup 100 for total conventional hip replacement, in addition to the foregoing, is its snap-fitting ability. Such is generally provided through hood 129, which provides for a greater than hemispherical embrace of the corresponding femoral component ball implant. However, as mentioned herein, with the cut-outs 126, a stable, full range of motion is not compromised by the snap-fit-providing hood 129.

Rim projection 129 delineats the socket implant of the invention can be made of any suitable material which, however, preferably is made of plastic. Advantageously, the socket implant of the invention is UHMWPE.

Figure 3:
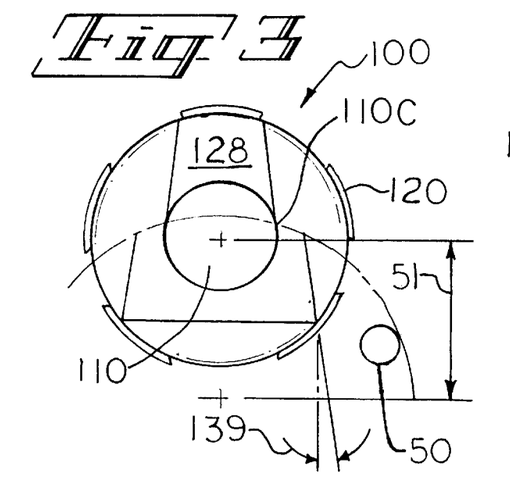
FIG. 3 is a bottom plan view of the cup of FIG. 1, at a stage of incomplete construction, looking into its ball-receiving cup.
Figure 4:
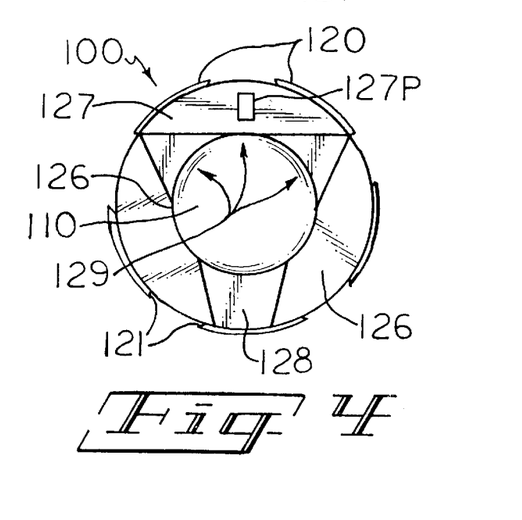
FIG. 4 is a bottom view of the cup of FIG. 1, completed.

In general, the cup 100, 200 is made by known methods. In particular, the UHMWPE cup 100, 200 is made by methods which include computer-assisted machining and cutting of a UHMWPE blank, which, for example, may employ a 0.375-inch ballnose cutter 50; a 1.528-inch length 51 may be referenced (FIG. 3). Sterilization of the socket implant typically follows.

Figure 1:
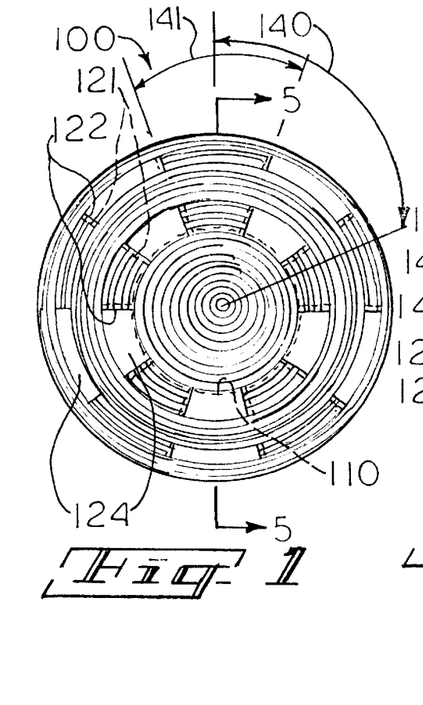
FIG. 1 is a top plan view of an enarthrodial type socket implant of the invention, embodied as acetabular cup, particularly adapted for a human cotyloid cavity, i.e., acetabulum, for conventional total hip replacement.
Figure 2:
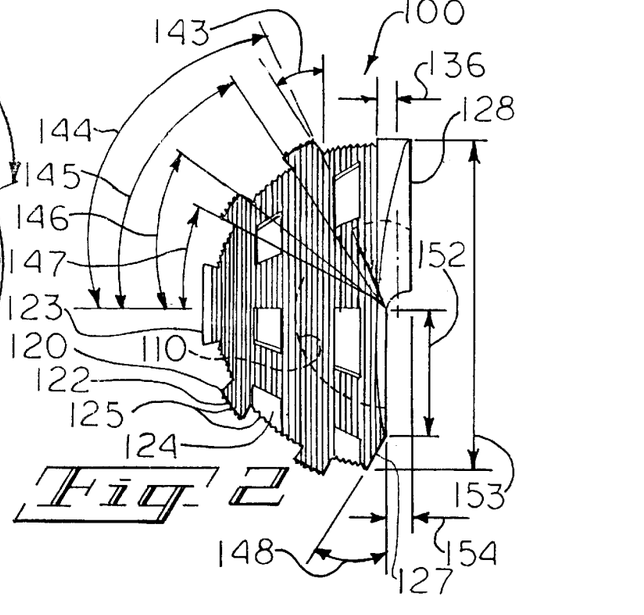
FIG. 2 is a side plan view of the cup of FIG. 1.
Figures 5, 6, 7:
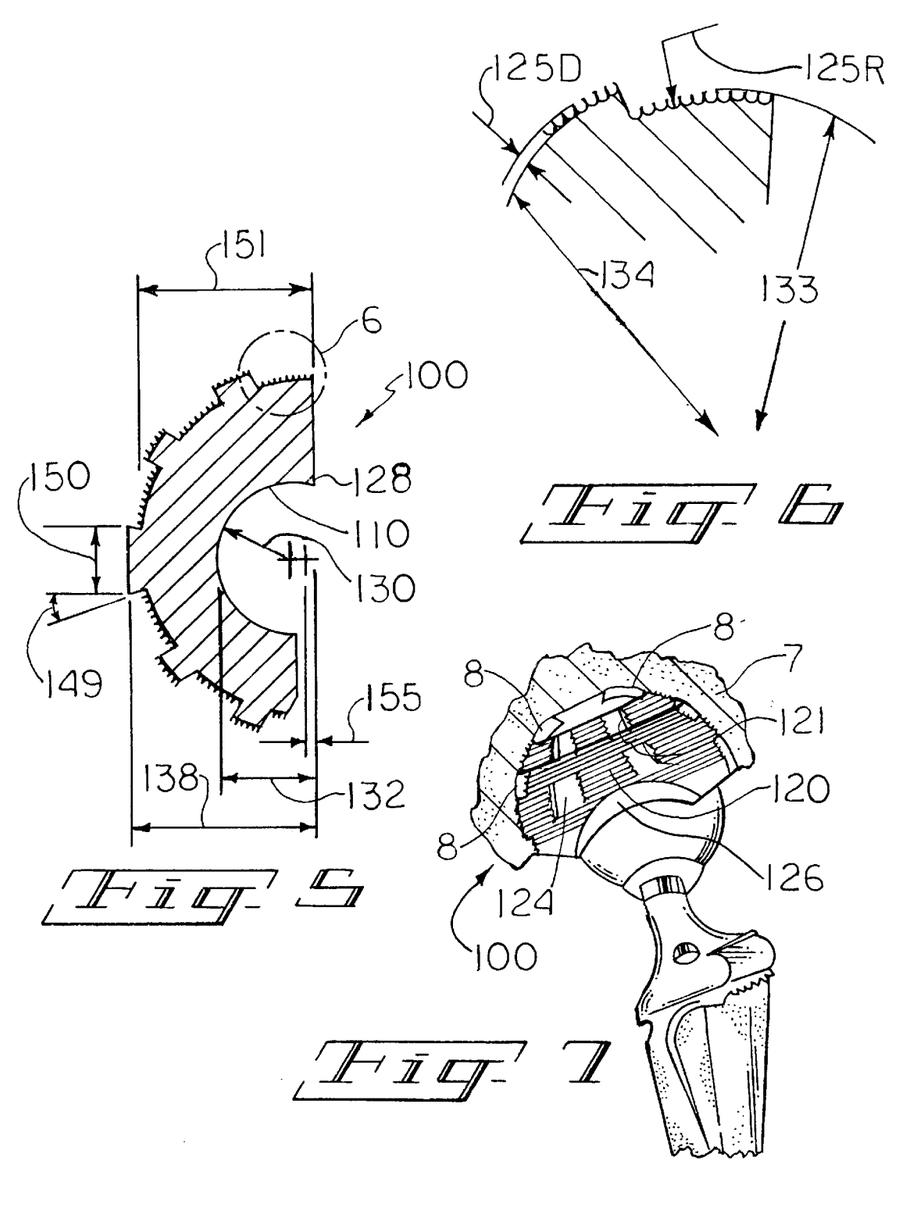
FIG. 5 is a sectional view of the cup of FIG. 1, taken along 5—5 as depicted in FIG. 1.
FIG. 6 is a detailed sectional view of a portion of the cup as depicted in FIG. 5, taken from within the detail circle 6.
FIG. 7 is a side plan view of the cup of FIG. 1, receiving a corresponding conventional femoral ball from below, and stably cemented to suitable hip bone stock, which is shown in section.
Figures 8, 9, 10:
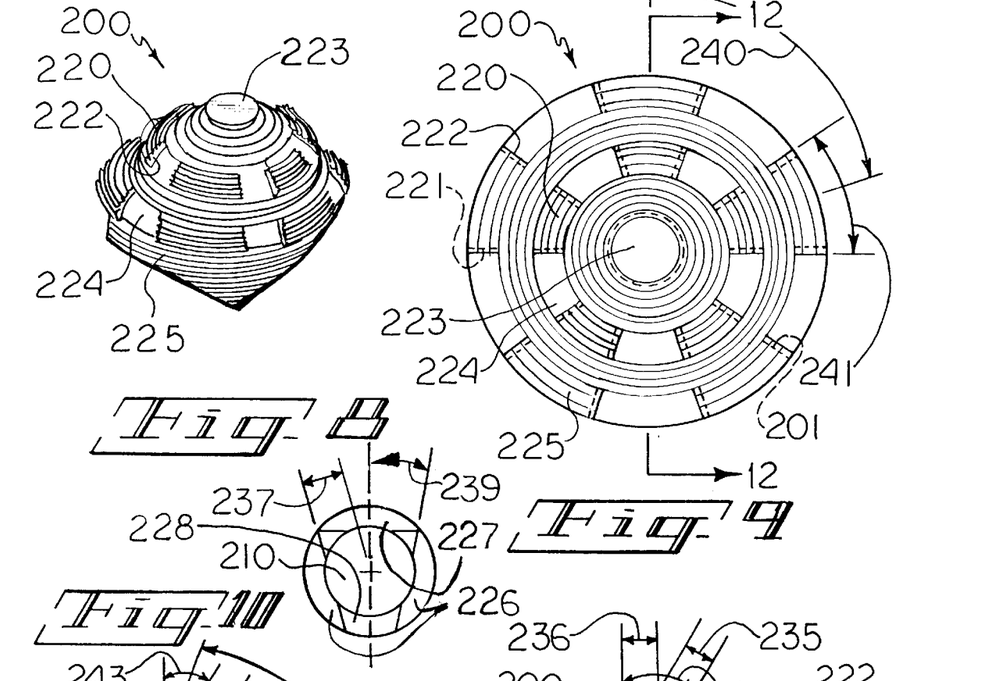
FIG. 8 is a back (top) perspective view of another enarthrodial type socket implant of the invention, embodied as an acetabular cup, particularly adapted for the human acetabulum and for a TARA procedure.
FIG. 9 is a top view of the cup of FIG. 8.
FIG. 10 is a bottom view of the cup of FIG. 8, looking into its ball-receiving cup.

Dimensions of the head-receiving cup may vary as needed for a particular application. For instance, with the UHMWPE acetabular head-receiving cup 100 component as a prosthetic part of a total conventional hip joint, the cup 200 can be supplied in several femoral ball accommodating dimensions, for example, in 28-mm and 32-mm dimensions, and, for further example, the following dimensions listed in inches, with ±0.010-inch tolerances unless otherwise noted, may be encountered in total conventional replacement joints sized in millimeters (mm) with the UHMWPE cup 100, for the 28-mm size ball-receiving cup 110 (FIGS. 1, 2 & 5):

| Feature/No. | 46-mm | 48-mm | 50-mm | 52-mm | 54-mm | 56-nm | 58-mm |
|---|---|---|---|---|---|---|---|
| 130 | 0.633 | 0.633 | 0.633 | 0.633 | 0.633 | 0.633 | 0.633 |
| 131 | 0.292 | 0.264 | 0.231 | 0.192 | 0.152 | 0.112 | 0.073 |
| 132 | 0.735 | 0.752 | 0.762 | 0.762 | 0.762 | 0.762 | 0.762 |
| 133 | 0.828 | 0.867 | 0.906 | 0.945 | 0.985 | 1.025 | 1.064 |
| 134 | 0.886 ± 0.20 | 0.925 ± 0.20 | 0.964 ± 0.20 | 1.003 ± 0.20 | 1.043 ± 0.20 | 1.083 ± 0.20 | 1.122 ± 0.20 |
| 136 | 0.118 | 0.118 | 0.118 | 0.080 | 0.080 | 0.080 | 0.080 |
| 138 | 1.198 | 1.209 | 1.215 | 1.215 | 1.215 | 1.215 | 1.215 |
| 151 | 1.120 | 1.131 | 1.137 | 1.137 | 1.137 | 1.137 | 1.137 |
| 152 | 0.479 | 0.507 | 0.549 | 0.577 | 0.606 | 0.649 | 0.678 |
| 153 | 1.639 | 1.718 | 1.796 | 1.883 | 1.963 | 2.004 | 2.122 |
| 154 | 0.118 | 0.118 | 0.118 | 0.117 | 0.117 | 0.117 | 0.117 |
| 155 | 0.292 | 0.264 | 0.231 | 0.192 | 0.152 | 0.112 | 0.073 |
| Plunge Depth | 0.272 | 0.278 | 0.276 | 0.283 | 0.289 | 0.288 | 0.293 | dimensions 130, 133 & 134 are spherical radii, and dimension 153 refers to that dimension before cutting side angles;

and the following dimensions in inches, with ±0.010-inch tolerances unless otherwise noted, may be encountered in total conventional replacement joints sized in millimeters (mm) with the UHMWPE cup 100, for the 32-mm size ball-receiving cup 110 (FIGS. 1, 2 & 5):

| Feature/No. | 50-mm | 52-mm | 54-mm | 56-mm | 58-mm |
|---|---|---|---|---|---|
| 130 | 0.639 | 0.639 | 0.639 | 0.639 | 0.639 |
| 131 | 0.214 | 0.186 | 0.152 | 0.112 | 0.073 |
| 132 | 0.824 | 0.835 | 0.841 | 0.841 | 0.841 |
| 133 | 0.906 | 0.945 | 0.985 | 1.025 | 1.064 |
| 134 | 0.964 | 1.003 | 1.043 | 1.083 | 1.122 |
|  | ±0.20 | ±0.20 | ±0.20 | ±0.20 | ±0.20 |
| 136 | 0.118 | 0.080 | 0.080 | 0.080 | 0.080 |
| 138 | 1.198 | 1.209 | 1.215 | 1.215 | 1.215 |
| 151 | 1.120 | 1.131 | 1.137 | 1.137 | 1.137 |
| 152 | 0.549 | 0.577 | 0.606 | 0.649 | 0.678 |
| 153 | 1.796 | 1.883 | 1.963 | 2.004 | 2.122 |
| 154 | 0.118 | 0.117 | 0.117 | 0.117 | 0.117 |
| 155 | 0.214 | 0.186 | 0.152 | 0.112 | 0.073 |
| Plunge Depth | 0.276 | 0.283 | 0.289 | 0.288 | 0.293 |

Continuing further, for instance, with the UHMWPE acetabular head-receiving cup 200 component as a prosthetic part of a TARA hip joint, the cup 200 can be supplied in several dimensions of thickness, for example, in 6-mm and 7-mm thicknesses, and, for further example, the following dimensions listed in inches, with ±0.010-inch tolerances unless otherwise noted, may be encountered in some total femoral resurfacing replacement joints sized in millimeters (e.g., 38×52) with the UHMWPE cup 200 (FIGS. 9–12):

Various other sized cups can be made in the practice hereof.

The cups of the invention can be implanted by generally known surgical methods. A suitable surgical cement is employed.

CONCLUSION

The present invention is thus provided. Various combinations and subcombinations and features may be practiced with or without reference to other combinations, subcombinations and/or features, alone or in combination, in the practice of the invention, and, moreover, numerous further adaptations and modifications can be effected within its spirit, the literal claim scope of which is particularly pointed out as follows.

Figure 11:
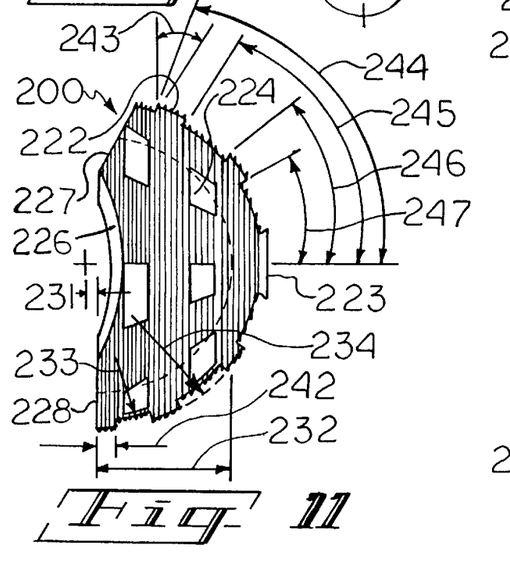
FIG. 11 is a side view of the cup of FIG. 8.
Figure 12:
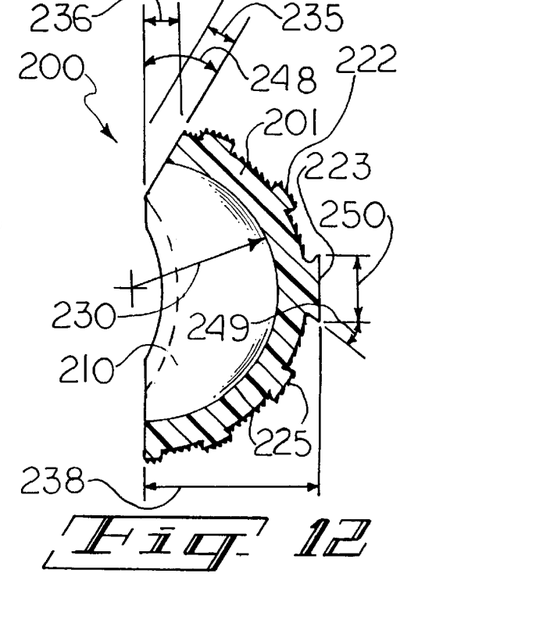
FIG. 12 is a sectional view of the cup of FIG. 8, taken along 12—12 as depicted in FIG. 8.

I claim:

1. A head-receiving cup for a ball and socket joint implant, said cup comprising a body, an articular surface and a mountable back surface, the articular surface of which, when the head-receiving cup is suitably mounted in suitable receiving stock, mates in gliding contact with a smooth external surface of a corresponding ball joint head of a ball and socket head-containinq joint component when said corresponding component is also suitably mounted in suitable receiving stock, and the mountable back surface being generally partially spherical and including small, widely dispersed cement spacer elevation members extending from the back surface to provide for an appropriately thick cement mantle and intended to assure an optimally proficient, implant-stabilizing cement mantle which is universally consistent and technically routine to implant,

| No. | 38 × 52 | 41 × 55 | 43 × 57 | 43 × 59 | 45 × 59 | 45 × 61 | 47 × 61 | 47 × 63 |
|---|---|---|---|---|---|---|---|---|
| 230 | 0.756 | 0.815 | 0.855 | 0.855 | 0.895 | 0.895 | 0.934 | 0.934 |
| 231 | 0.009 | 0.018 | 0.028 | 0.028 | 0.038 | 0.038 | 0.048 | 0.048 |
| 232 | 0.747 | 0.797 | 0.827 | 0.827 | 0.857 | 0.857 | 0.886 | 0.886 |
| 233 | 0.985 | 1.044 | 1.083 | 1.122 | 1.122 | 1.162 | 1.162 | 1.201 |
| 234 | 1.004 ± | 1.063 ± | 1.102 ± | 1.141 ± | 1.141 ± | 1.181 ± | 1.181 ± | 1.220 ± |
|  | 0.020 | 0.020 | 0.020 | 0.020 | 0.020 | 0.020 | 0.020 | 0.020 |
| 235 | 0.131 | 0.140 | 0.145 | 0.151 | 0.151 | 0.157 | 0.157 | 0.172 |
| 236 | 0.151 | 0.162 | 0.167 | 0.174 | 0.174 | 0.181 | 0.181 | 0.199 |
| 237 | 0.723 | 0.764 | 0.792 | 0.820 | 0.820 | 0.848 | 0.848 | 0.875 |
| 238 | 1.024 | 1.083 | 1.122 | 1.161 | 1.161 | 1.240 | 1.201 | 1.240 | and common among the foregoing particularly sized cups 200 is the typical dimension for feature 242 of 0.080±0.020 inch (FIG. 11).

Common to both foregoing particularly sized cups 100 & 200 are the following typical dimensions (FIGS. 1–3 & 5 and 9–12):

| Numbers | Value |
|---|---|
| 139, 239 | 10 ± 1 - degree angle. |
| 140, 240 | 72 ± 1 - degree angle. |
| 141, 241 | 36 ± 1 - degree angle. |
| 143, 243 | 27 ± 1 - degree angle. |
| 144, 244 | 70 ± 1 - degree angle. |
| 145, 245 | 60 ± 1 - degree angle. |
| 146, 246 | 40 ± 1 - degree angle. |
| 147, 247 | 30 ± 1 - degree angle. |
| 148, 248 | 30 ± 0.1 - degree angle. |
| 149, 249 | 15 ± 1 - degree angle. |
| 150, 250 | 0.425 ± 0.005 - inch dimension. | wherein:

said spacer elevation members include:

an elevated block or button centrally positioned on and extending from the back surface; and a plurality of rectangularly-shaped members in block form to provide a block top and side walls, said block top having a series of grooves thereon, said side walls being angled such that said members are dove tailed, and said plurality of members oriented in a series of concentric rows in relation to said elevated block or button; and there are, concentrically bordering each series of rows of rectangularly-shaped members, areas of the back surface having a series of grooves; and said cup is monolithically made from plastic.

2. The cup of claim 1, wherein the grooves of said rectangularly-shaped cement spacer elevation members and concentrically bordering areas of the back surface are concentrically oriented with respect to said elevated block or button.

3. The cup of claim 1, which is not snap-fitting to a corresponding mating ball and which is adapted for total articular resurfacing arthroplasty.

4. The cup of claim 2, which is not snap-fitting to a corresponding mating ball and which is adapted for total articular resurfacing arthroplasty.

5. The cup of claim 3, which is an acetabular cup for total hip resurfacing arthroplasty.

6. The cup of claim 4, which is an acetabular cup for total hip resurfacing arthroplasty.

7. The cup of claim 5, which is made of UHMWPE.

8. The cup of claim 6, which is made of UHMWPE.

9. A head-receiving acetabular cup for a ball and socket hip joint implant, said cup comprising a body, an articular surface and a mountable back surface, said cup being monolithically made from plastic, the articular surface of which, when the head-receiving cup is suitably mounted in suitable receiving stock, mates in gliding contact with a smooth external surface of a corresponding ball joint head of a ball and socket head-containing femoral joint component when said corresponding component is also suitably mounted in suitable receiving stock; said body including:

generally opposing, angled cut-out margins to antero-inferior and postero-inferior marginal rim extensions of said body which can accommodate an anterior anatomical indentation of hip socket containment and engender avoidance of premature abutment of a postero-inferior aspect of the margin against an opposing femoral neck of said femoral joint component or an opposing femoral bone neck, with external rotation and/or adduction of the hip, which allow a normal, non-dislocating range of unobstructed external and internal rotation of the hip joint; and the mountable back surface being generally partially spherical and including small, widely dispersed cement spacer elevation members extending from the back surface to provide for an appropriately thick cement mantle and intended to assure an optimally proficient implant-stabilizing cement mantle which is universally consistent and technically routine to implant, said spacer elevation members including:

an elevated block or button centrally positioned on and extending from the back surface; and a plurality of rectangularly-shaped members in block form to provide a block top and side walls, said block top having a series of grooves thereon, said side walls being angled such that said members are dove tailed, and said plurality of members oriented in a series of concentric rows in relation to said elevated block or button;

and there are, concentrically bordering each series of rows of rectangularly-shaped members, areas of the back surface having a series of grooves.

10. The cup of claim 9, further including an angled top margin between top portions of said generally opposing angled cut-outs.

11. The cup of claim 10, which is made of UHMWPE and which is for total hip resurfacing arthroplasty, wherein the grooves of said rectangularly-shaped cement spacer elevation members and concentrically bordering areas of the back surface are concentrically oriented with respect to said elevated block or button.

12. A head-receiving acetabular cup for a ball and socket hip joint implant, said cup comprising a body, an articular surface and a mountable back surface, said cup being monolithically made from plastic and being for total, conventional hip replacement arthroplasty, the articular surface of which, when the head-receiving cup is suitably mounted in suitable receiving stock, mates in gliding contact with a smooth external surface of a corresponding ball joint head of a ball and socket head-containing femoral joint component when said corresponding component is also suitably mounted in suitable receiving stock; said body including:

generally opposing, angled cut-out margins to antero-inferior and postero-inferior marginal rim extensions of said body which can accommodate an anterior anatomical indentation of hip socket containment and engender avoidance of premature abutment of a postero-inferior aspect of the margin against an opposing femoral neck of said femoral joint component, with external rotation and/or adduction of the hip, which allow a normal, non-dislocating range of unobstructed external and internal rotation of the hip joint; and the mountable back surface being generally partially spherical and including small, widely dispersed cement spacer elevation members extending from the back surface to provide for an appropriately thick cement mantle and intended to assure an optimally proficient, implant-stabilizing cement mantle which is universally consistent and technically routine to implant, said spacer elevation members including:

an elevated block or button centrally positioned on and extending from the back surface; and a plurality of rectangularly-shaped members in block form to provide a block top and side walls, said block top having a series of grooves thereon, said side walls being angled such that said members are dove tailed, and said plurality of members oriented in a series of concentric rows in relation to said elevated block or button; and there are, concentrically bordering each series of rows of rectangularly-shaped members, areas of the back surface having a series of grooves;

which cup further comprises a snap-fitted hood arrangement of the head-restraining marginal outlet of the acetabular cup which includes a marginally extended continuation of a superior one-half or so of cup containment that is of a sufficient magnitude to reduce an overall dimension of a socket outlet of the cup to less than a hemisphere and thus provide a greater than hemispherical embrace of the femoral head component.

13. The cup of claim 12, further including an angled top margin between top portions of said generally opposing angled cut-outs.

14. The cup of claim 13, wherein the grooves of said rectangularly-shaped cement spacer elevation members and concentrically bordering areas of the back surface are concentrically oriented with respect to said elevated block or button.

15. The cup of claim 12, which is made of UHMWPE.

16. The cup of claim 13, which is made of UHMPE.

17. The cup of claim 14, which is made of UHMWPE.

* * * * *

UNITED STATES PATENT AND TRADEMARK OFFICE
CERTIFICATE OF CORRECTION

PATENT NO. : 6,136,034
DATED : October 24, 2000
INVENTOR(S) : Charles O. Townley It is certified that error appears in the above-identified patent and that said Letters Patent is hereby corrected as shown below:

On the title/abstract page, under OTHER PUBLICATIONS, fourth line, after "re-published" delete "1997." Insert therefor -- March, 1998. --.

In column 1, line 16, between "the" and "to" insert -- limited depth --.

In column 1, line 17, delete "acetabular" and insert therefor -- acetabulum --.

In column 1, line 22, after "occur" insert a comma, and then insert -- which --.

In column 1, line 26, between "the" and "for" insert -- TARA procedure, --.

In column 3, line 30, delete "acetebular" and insert therefor -- acetabular --.

In column 3, line 43, after "consistent in" insert -- thickness --.

In column 4, line 30, before "expensive" insert -- an --.

In column 6, line 23, insert the following sentence after "implant." -- Note, elevated or thickened rim portion 128. --

In column 6, line 26, delete "Rim projection 129 delineats the" and insert therefor -- The --.

UNITED STATES PATENT AND TRADEMARK OFFICE
CERTIFICATE OF CORRECTION

PATENT NO. : 6,136,034
DATED : October 24, 2000
INVENTOR(S) : Charles O. Townley It is certified that error appears in the above-identified patent and that said Letters Patent is hereby corrected as shown below:

In column 6, line 40, delete "200" and insert therefor -- 100 --.

In column 8, line 23, delete "containinq" and insert therefor -- containing --.

In column 10, line 58, delete "UHMPE" and insert therefor -- UHMWPE --.

Signed and Sealed this

Eighth Day of May, 2001

Attest:

NICHOLAS P. GODICI

Attesting Officer    Acting Director of the United States Patent and Trademark Office